United States Patent
Dietz et al.

(12) 
(10) Patent No.: US 6,552,784 B1
(45) Date of Patent: Apr. 22, 2003

(54) DISPOSABLE OPTICAL CUVETTE CARTRIDGE

(75) Inventors: Louis J. Dietz, Mountain View, CA (US); James L. Winkler, Sunnyvale, CA (US)

(73) Assignee: SurroMed, Inc., Palo Alto, CA (US)

( * ) Notice: Subject to any disclaimer, the term of this patent is extended or adjusted under 35 U.S.C. 154(b) by 0 days.

(21) Appl. No.: 09/552,872

(22) Filed: Apr. 20, 2000

Related U.S. Application Data

(60) Provisional application No. 60/130,876, filed on Apr. 23, 1999, provisional application No. 60/130,918, filed on Apr. 23, 1999, and provisional application No. 60/130,875, filed on Apr. 23, 1999.

(51) Int. Cl.[7] .......................... G01N 1/10; G01N 33/00; G01N 21/03; G01N 33/86; G01J 3/00
(52) U.S. Cl. ................. 356/246; 356/244; 356/300; 356/440; 422/56; 422/73; 422/102; 422/104; 436/69; 436/501; 436/526; 436/165; 250/576; 204/452
(58) Field of Search ................. 356/246, 244, 356/39, 300, 440, 445; 422/102, 104, 56, 72, 82.05, 82.09, 73; 436/501, 526, 69, 165, 180; 250/576; 204/452, 603; 200/310

(56) References Cited

U.S. PATENT DOCUMENTS

| | | | |
|---|---|---|---|
| 3,552,865 A | 1/1971 | Leung et al. | 356/246 |
| 3,690,836 A | 9/1972 | Buissier et al. | 422/56 |
| 4,405,235 A | 9/1983 | Rossiter | 356/246 |
| 4,643,570 A | 2/1987 | Maechler et al. | 356/246 |
| 4,761,381 A | 8/1988 | Blatt et al. | 436/165 |
| 4,963,498 A | 10/1990 | Hillman et al. | 436/69 |
| 5,430,542 A | 7/1995 | Shepherd | 356/246 |
| 6,133,046 A | * 10/2000 | Clerc | 436/501 |
| 6,200,532 B1 | * 3/2001 | Wu et al. | 422/73 |

FOREIGN PATENT DOCUMENTS

GB    1 407 247 A    9/1975

* cited by examiner

*Primary Examiner*—Loha Ben
(74) *Attorney, Agent, or Firm*—Swanson & Bratschun LLC

(57) ABSTRACT

A cuvette cartridge for optical measurements is disclosed herein, the cartridge comprising a flat, adhesive sheet having a selected thickness that defines an optical path length perpendicular to the longitudinal axis of such sheet; wherein a portion of the adhesive sheet is cut out to define at least one optical chamber of a desired length; wherein the adhesive sheet is placed between a first flat sheet and a second flat sheet, the first flat sheet comprising at least one inlet hole and at least one outlet hole, the vent hole being located at a first end of the optical chamber and the inlet hole being located at a second end of the optical chamber. An integrated analytical system employing this cartridge and optionally including a vacuum chuck for holding and registering the cartridge are also disclosed.

22 Claims, 3 Drawing Sheets

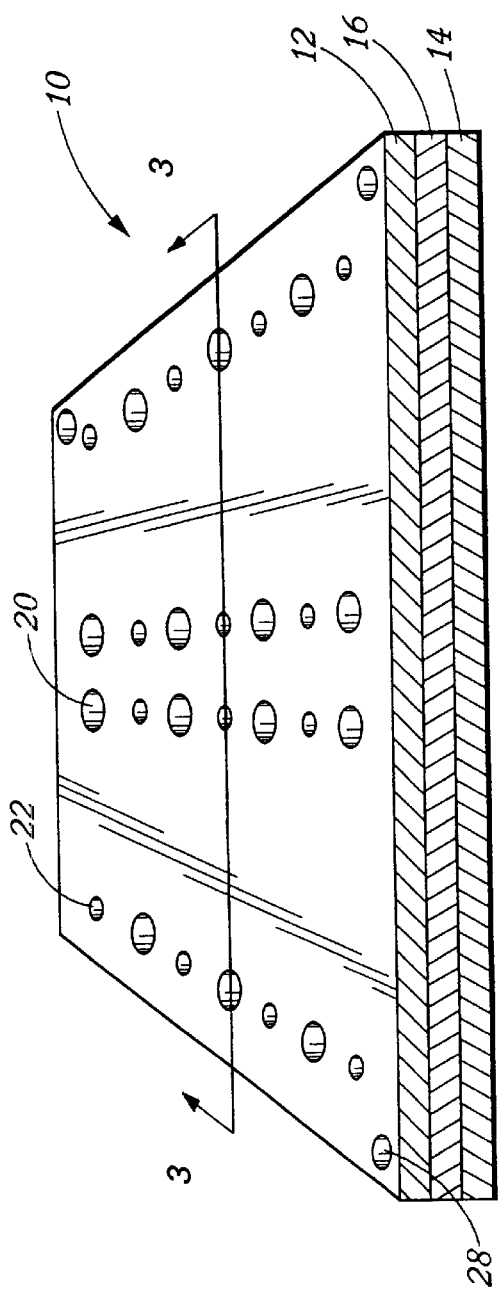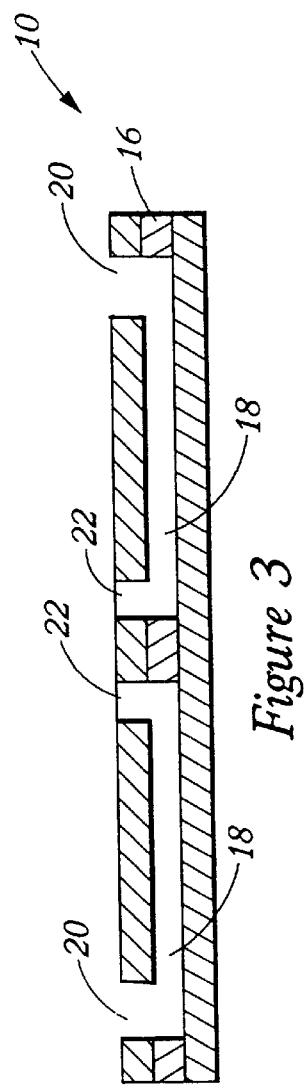

DISPOSABLE OPTICAL CUVETTE CARTRIDGE

RELATED APPLICATIONS

This application claims priority to U.S. Provisional Application No. 60/130,876, filed Apr. 23, 1999 entitled "Disposable Optical Cuvette Cartridge"; U.S. Provisional Application No. 60/130,918, filed Apr. 23, 1999, entitled "Spectrophotometric Analysis System Employing a Disposable Optical Cuvette Cartridge"; and U.S. Provisional Application No. 60/130,875, filed Apr. 23, 1999, entitled "Vacuum Chuck for Thin Film Optical Cuvette Cartridge."

FIELD OF THE INVENTION

The present invention relates to a disposable optical cuvette cartridge for spectrophotometric measurements of liquid samples such as whole blood, to methods for constructing the cuvette cartridge and to methods of using the cuvette cartridge.

BACKGROUND INFORMATION

U.S. Pat. No. 5,430,542 disclosed a cuvette comprising two optically transparent liquid-impermeable sheets, wherein a third adhesive sheet is inserted between the two transparent plastic sheets and the three sheets are pressure sealed together. The adhesive sheet had cut outs defining the contour of an optical chamber, inlet port, and vent port. A liquid sample to be analyzed was placed in the optical chamber through the inlet port in the adhesive layer and the thickness of the adhesive sheet defined the optical path length of the liquid sample within the cuvette.

SUMMARY OF THE INVENTION

It has now been found that the disposable optical cuvettes of the art are improved if the inlet port and vent port are present in and pass through one of the liquid-impermeable sheets rather than through the adhesive layer. The invention provides an improved disposable optical cuvette based upon this discovery for use in the spectrophotometric analysis of liquid samples, methods for manufacturing the improved cuvette as well as analytical systems and methods which employ the improved cuvette.

Thus, in a first aspect, this invention provides a cuvette cartridge for optical measurements of analytes in liquid samples. The cartridge comprises a flat, adhesive sheet having a selected thickness that defines an optical path length perpendicular to the plane of the flat sheet. A portion of the adhesive sheet is cut out to define at least one optical sample chamber of a desired length. The sample chamber is completed when the adhesive sheet is placed between and sealed to a first flat sheet and a second flat sheet. The first flat sheet contains a inlet hole and a vent hole which connect to the optical chamber. The vent hole is located at one end of the optical chamber, and the inlet hole is located at a second end of the optical chamber so that liquid can fill the sample chamber. In preferred embodiments, the cuvette cartridge contains a plurality of optical chambers each with its own inlet hole and vent hole.

In another aspect, the invention provides a disposable optical cuvette cartridge for use in the spectrophotometric analysis of liquid samples which employs a pair of parallel sheets of material impermeable to the liquid samples. The two sheets are held in spaced relationship to one another by an intermediate layer which has at least one discontinuity defining a sample zone having a thickness set by the spaced relationship between the two sheets. At least one of these two sheets is optically transparent at the wavelengths of the spectrophotometric analysis and one of the two sheets carries an inlet port and a vent port for each of the sample zones. The thickness of the intermediate layer defines the optical path through the sample zone and the quantity of sample presented for analysis. The thickness of the intermediate layer is also selected taking into account the hydrophilicity of the materials of the various layers to permit capillary action to draw the liquid sample into the sample zone when the sample is placed at the inlet port.

In yet another aspect, the invention provides a method of manufacturing a thin film disposable cuvette cartridge for use in the spectrophotometric analysis of liquid samples. This method involves sealably bonding three flat layers to one another in parallel alignment. The first and third layers are flexible sheets of thin film material impermeable to the liquid samples. The intermediate second layer is also made from a material which is impermeable to the liquid samples. This layer, which has a thickness which is preselected to provide a desired spacing between the first and third films following bonding, has at least one discontinuity. These discontinuities in the intermediate layer define at least one sample zone having a thickness set by the spaced relationship between the two sheets. At least one of the first and third sheets is optically transparent at the wavelengths employed in the spectrophotometric analysis and one of these two sheets carries an inlet port and a vent port for each of the sample zones. The thickness of the intermediate layer defines the optical path through the sample zones and is sized to cause capillary action to draw the liquid sample into the sample zone when the sample is placed at the inlet port.

In yet an additional aspect, the invention provides an integrated system for the spectrophotometric analysis of liquid samples. This system includes a cuvette cartridge into which liquid samples are placed for optical measurements of analytes, an excitation laser, capable of exciting fluorescence in the analytes, and a fluorescence detector capable of detecting the fluorescence excited in the analyte and providing information concerning the presence of the analyte based on the detected fluorescence. The cartridge comprises a flat, adhesive sheet having a selected thickness that defines an optical path length perpendicular to the plane of the flat sheet. A portion of the adhesive sheet is cut out to define at least one optical sample chamber of a desired length. The sample chamber is completed when the adhesive sheet is placed between and sealed to a first flat sheet and a second flat sheet. The first flat sheet contains a inlet hole and a vent hole which connect to the optical chamber. The vent hole is located at one end of the optical chamber, and the inlet hole is located at a second end of the optical chamber so that liquid can fill the sample chamber. The excitation laser is focused on the sample in the optical sample chamber and the fluorescence is detected from the chamber.

The invention also provides an apparatus for firmly holding the disposable thin film optical cuvette cartridge for use in the spectrophotometric analysis of liquid samples in a flattened and registered position as is generally preferred for spectrophotometric analysis of samples contained within the cuvette cartridge. This apparatus is a vacuum chuck which is specifically adapted to work with a cassette cartridge that itself includes a pair of parallel sheets of material impermeable to the liquid samples. The two sheets are held in spaced relationship to one another by an intermediate layer which has at least one discontinuity defining a sample zone having a thickness set by the spaced relationship between the two sheets. At least one of these two sheets is optically transparent at the wavelengths of the spectrophotometric analysis. At least two locating pin holes pass through the two sheets and the intermediate layer.

The vacuum chuck has a continuous perimeter which is shaped to surround the sample zone when a cuvette cartridge is placed upon it and has additional areas within the perimeter. The perimeter and the additional areas are coplanar and define a flat planar surface upon which the cuvette cartridge may be placed. The flat planar surface has indentations extending below the surface defined by the perimeter and the additional areas. These indentations are located beneath the sample zones when the cuvette cartridge is placed on the chuck. The chuck can also present features for accurately registering the cuvette cassette. These can include pins, ridges or other barriers which engage the cassette or markers that may be read by automated registration equipment, or the like. In the embodiment shown in the drawings, the chuck has at least two pins extending upwards from the planar surface and located in the planar surface so as to engage the at least two locating pin holes present in the cuvette cassette. The chuck includes a vacuum source connected to the indentations to apply a vacuum thereto to pull the cuvette cartridge into a locked and registered flat position on the planar surface when the locating pin holes of the cassette are mated with the pins of the chuck.

BRIEF DESCRIPTION OF THE DRAWINGS

This invention will be further described with reference being made to the accompanying drawings in which:

FIG. 2 is a perspective not-to-scale view of an assembled cassette cartridge of this invention;

FIG. 3 is a cross-sectional view at 3—3 of the assembled cassette cartridge of FIG. 2.

DETAILED DESCRIPTION OF THE INVENTION

Figure 1:
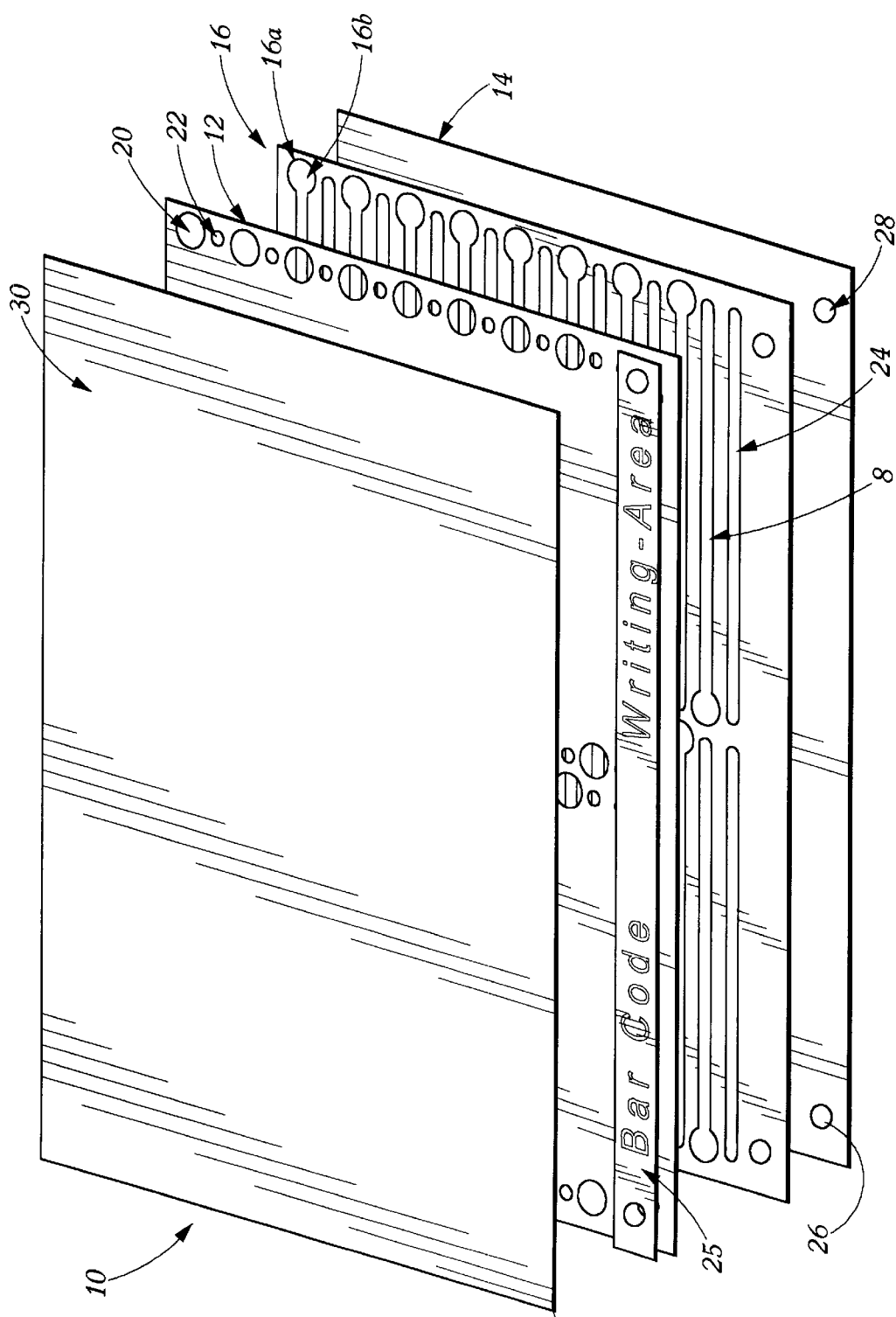
FIG. 1 is a generally schematic exploded perspective view of a cassette cartridge of this invention.
Figure 4:
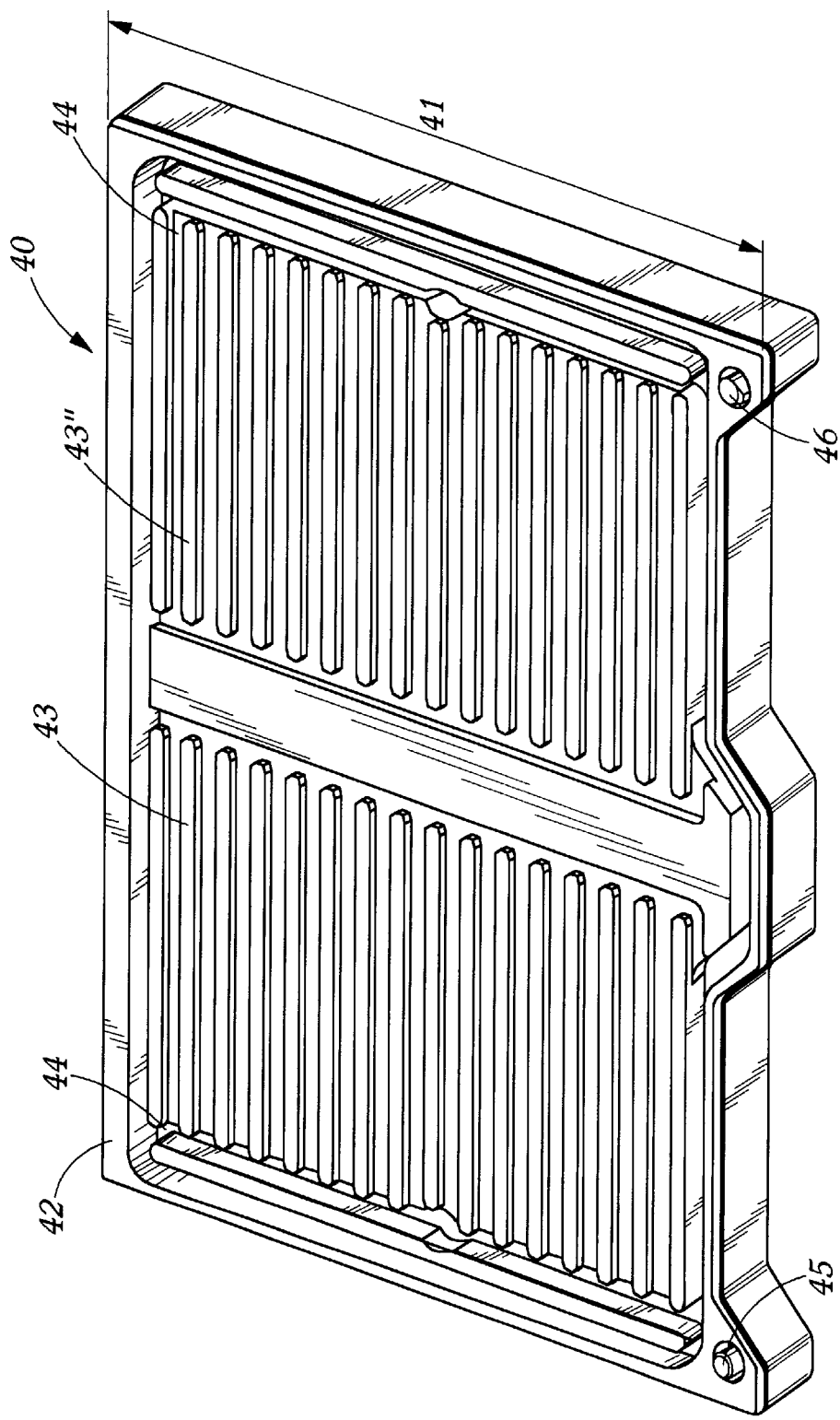
FIG. 4 is a perspective view of a vacuum chuck which can be used to hold the cassette cartridge in position in use in the analysis of liquid samples.

Referring to FIGS. 1, 2 and 3, an optical cuvette cartridge is shown generally at 10. Optical cuvette cartridge 10 comprises two substantially flat sheets 12 and 14. These sheets are "liquid impermeable" which term denotes that they contain and are not affected by the liquid samples which are placed in the cuvette cassette for analysis. One, and more typically both, of these sheets are "transparent" which term denotes that the sheets are substantially optically transmissive and transmit a substantial amount, such as at least about 25% and preferably at least about 50%, of light shone upon them at the wavelengths which are relevant to their use as sample cuvettes in spectrophotometric analysis settings.

Sheets 12 and 14 are preferably flexible, nonrigid plastic films. Since many of the spectrophotometric analysis techniques which are carried out using the cuvette cassettes of this invention involve laser stimulation of fluorescence in the samples, preferably, the material used to make these plastic films has a low fluorescence in the ranges which would interfere with the signals of interest to the user.

Poly(ester)s including poly(ethylene terephthalate) and other terephthalate ester polymers, poly(urethane)s, cellulose polymers, acrylic polymers, poly(carbonate)s, poly (styrene) and poly(vinyl fluoride)s are representative examples of the types of materials which can be used for sheets 12 and 14. Sheets 12 and 14 are "thin films" which denotes that they are from about 0.25 mils (6 microns) to about 25 or even 100 mils or more in thickness. Preferred embodiments of the present invention use sheets of polyesters, and especially poly(ethylene terephthalate) glycol from 0.5 mils to about 25 mils, and particularly 10 mils or so in thickness. These materials are available commercially from ICI, duPont, and the like under trademarks and tradenames such as Mylar®, Melinex®, Melinex® 725 (duPont) and the like.

The surface tension of sheets 12 and 14 is generally important. The surface tension of plastic sheets is reflected in the degree of wettability ("hydrophilicity") that the sheets process. Many of the plastics having optical properties which are useful in the cuvette cassettes may present high surface tensions and hence low levels of hydrophilicity which render them unacceptable for use, because they resist wetting by the aqueous liquid samples and thus do not permit the aqueous liquid samples to be drawn into the sample zone. As is well understood in the art, the surface tension of a plastic film can be altered by chemically treating the surface of the film with a surface tension lowering agent, by physically modifying the surface or by plasma treating the surface. Any of these treatments may be employed to provide surfaces with levels of hydrophilicity adequate to permit the aqueous liquid samples to be drawn into the sample zone.

Although the sheets are shown to be in substantially rectangular form in the embodiment shown in the drawings, the actual shape may be varied to adapt the resulting cuvette cassette to fit the spectrophotometric analysis apparatus.

Sheets 12 and 14 are spaced apart from one another but adhesively secured together by an intermediate layer 16. Layer 16 has one or more discontinuities 16a which are areas where the layer 16 has been cut away or is otherwise not present. These areas provide sample zones having an optical path length corresponding to the thickness of layer 16, which for the purposes of the present explanation is preferably about 50 to about 200 microns, preferably 75 to about 175 microns and more preferably about 125 microns.

Layer 16 can be provided by an accurately laid down layer of a dimensionally-stable adhesive such as the pressure-sensitive acrylic adhesives and pressure-sensitive butylene polymer adhesives, silicone adhesives, hot melt thermoplastic adhesives and the like which is printed upon one of the sheets 12 or 14 in a pattern which provides the desired discontinuities. Such printing can be carried out using conventional techniques including silk screening, lithography, printing from an "x-y" adhesive dispenser and the like. In this case the layer 16 is printed upon one of sheets 12 and 14 and thereafter the second of sheets 12 and 14 is laminated on top of layer 16. The adhesive can be laid down as a liquid or as a semisolid. It can be partially cured in place before the additional layers are laminated to it. It could also be cured in place after the top and bottom layers are in place as long as care is taken to maintain the proper spacing between the layers (such as by the placement of spacer elements) and to assure that the integrity of the discontinuities which define the sample zones is maintained. Curing can be effected by light, heat, or ultraviolet radiation or the like depending upon the particular adhesive employed.

More typically at this time, layer 16 is a preformed sheet of adhesive or a preformed sheet of adhesive-coated polymer which is adhered to sheets 12 and 14. Alternatively, layer 16 could be a sheet of heat-sealable polymer film which is heat sealed or otherwise laminated between sheets 12 and 14. Any adhesive which will bond to the polymer films, which will not be adversely affected by or which will not itself affect the typically aqueous liquid samples can be used. These include acrylic adhesives, cyanoacrylates, silicones, epoxies, esters, poly(olefin)-based adhesives and the like. In a particularly preferred embodiment, layer 16 is a double-sided adhesive sheet, preferably a material such as Arclad® 8482 (Adhesives Research, Inc.) or other similar acrylic-based film.

Although not a requirement, it is often advantageous if the material of the intermediate layer 16 has spectrophotometric properties which are distinguishable from those of layers 12 and 14. By noting the difference in properties, one can determine accurately when the spectrophotometer is reading the spectrophotometric profile of the sample and when it is reading information for areas outside the sample zone. Similarly, sophisticated automated spectrophotometric readers can locate the edges of the sample zone by noting the properties of layer 16 and make their readings on the contents of the sample zone safely away from the edges.

The sample zones present in the discontinuities in layer 16 are each accessed by a pair of openings present in sheet 12. One of these, inlet hole 20, is at one end or side of the sample zone and the other, vent hole 22, is spaced away from it at the other end or side of the sample zone.

The method of construction of cuvette cartridge 10 when layer 16 is itself a polymer film, involves the cutting, such as but not limited to laser, rotary or matched metal pattern die cutting, of the double-backed adhesive sheet 16 as indicated at 16a, to provide a readily removable piece 16b, having the desired contour of an optical chamber 18. Inlet hole 20 and vent hole 22 are cut into flat sheet 12, for example by punching.

The adhesive 16 sheet is then applied to one of the flat sheets 12 and 14 and the removable cut piece 16b is then peeled off. The other flat sheet is then applied over the adhesive sheet 16. The remainder of the adhesive sheet 16 will hold the two transparent flat sheets together providing a liquid tight seal and will form an optical chamber of defined volume, shape, and optical path length. Inlet hole 20 is generated by the placement of the flat sheet 12 over the adhesive sheet 14 such that the inlet hole 20 located at one end of the optical chamber 18 and outlet or vent hole 20 is located at the other end of the optical chamber.

In use, a drop, which will typically range from about 5 to 50 microliters, more preferably about 15 microliters, of a liquid sample is placed on the inlet hole 20. Surface tension holds the drop on the hole and capillary action brought about by the cross-section of the sample zone 18 draws the sample into the zone 18 and fills it completely, with excess sample remaining at the inlet hole 20. This obviates the need for a well of a defined volume or for accurate measurement of the volume of the drop applied to the hole.

One advantage of the cuvette cartridge of this invention is its ability to incorporate a plurality of sample zones in a single unit. Thus, while the cassette can include a single sample zone 18, preferably two to about 500 optical chambers 18 are provided in a single cuvette cartridge assembly. Certainly, the sample cassette can include many more than 500 optical chambers, if desired. As various types of automated sample handling equipment are perfected, the density of sample zones can increase dramatically. The present invention will find excellent application in such settings.

In many present applications there is a preference for the cassette to have from about 8 to about 100 and especially, from about 30 to 50 optical chambers. Referring generally to FIGS. 1–3, this multiplicity of optical chambers is provided by locating the desired number of removable-pieces 16b on the adhesive sheet and a corresponding number of inlet and vent holes on flat sheet 12. The inlet and vent holes may be staggered or arranged in an antiparallel orientation as indicated in FIG. 1 to provide, for example, closer spacing of optical chambers on the flat sheet. In an embodiment, the center to center spacing of inlet holes is about nine millimeters for ease in filling with a multichannel pipette.

In some embodiments, at least one additional optical chamber 24 may be provided in the cartridge as a reference or calibration aide as described below. This reference optical chamber may optionally lack inlet hole 20 and/or outlet hole 22 and is provided to remain empty and serve as a calibration blank or to contain a calibration solution or other standard the measurement of which can be used in the accurate determination of the analyte in the samples.

Bar code 25 or other labels may be added to the assembly, preferably on flat sheet 12, in a location adjacent to the optical chambers so as not to obscure measurement of the samples in the optical chambers.

In some embodiments, pinholes 26 and 28 may be provided to assist in the registration of the cartridge on a platform during an optical measurement. Such pinholes are sized to engage locating pins present in the optical measurement system and will typically range from about 1/32 to about 1/4 inch, preferably about 0.125 inch, in size and may optionally be located in all three layers of the cartridge so as to provide a hole through the entire thickness of the three layers.

In typical use, the inlet holes are filled with a liquid sample, such as but not limited to blood, serum, urine, saliva, homogenate of cells or tissue, suspension or cells or tissue or constituents thereof, or analytes in a reaction mixture, or solution of analytes, or combination thereof. One or more optical chambers may be filled with a control sample, such as a solution of a dye of desired optical properties. A cover 30 may be placed over the flat sheet 12 after filling of the inlet ports to reduce evaporation of the samples or other loss. Cover 30 is preferably fabricated out of the same materials as flat sheets 12 or 14. The inlet ports may also be covered with a tape or other material to prevent sample evaporation. The tape or other material should be applied so as not to obscure measurement of the sample in the optical chamber.

It will be appreciated that the disposable thin-film cuvette cartridges with their extremely small sample volumes and their flexible construction could require very precise spectrophotometric measurement methodologies to give accurate information concerning the samples. To this end it can be important to accurately and positively position the thin-film cassette in the spectrophotometric measurement apparatus.

In one embodiment, the thin-film cassette cartridge is placed on a support such as a vacuum chuck, which can hold the cassette in accurate registration and in a very well-defined profile, such as a very flat profile. Such a vacuum chuck is shown generally in FIG. 2. Chuck 40 presents a generally flat top surface 41 which includes a continuous perimeter 42, a series of raised areas 43, which together with perimeter 42, make up a flat surface upon which the thin film cassette is placed. Top surface 41 also includes a series of depressed areas 44 which are below the plane defined by perimeter 42 and raised areas 43. When cassette 10 is paced onto this chuck, pinholes 26 and 28 in the cassette are aligned with pins 45 and 46 to accurately register the cassette. A vacuum is applied to the volume defined by depressed area 44. This pulls the cassette down onto the chuck and seals it firmly onto the plane defined by raised areas 43 and perimeter 42.

This vacuum chuck 40 is fabricated out of a material such as metal, plastic, glass, ceramic, and so on which is stable and nonreactive with the sample cassette and preferably with the aqueous samples. In one embodiment the vacuum chuck may be mounted on an optical measurement device such as a laser fluorescence scanner. Use of such a vacuum chuck is advantageous in that the cartridge is held flat against the chuck, thereby facilitating focusing of the optical instrument and reducing a need to refocus during measurements of multiple optical chambers on the cartridge. Furthermore, the use of a vacuum chuck to hold the cartridge flat obviates any requirement that the cartridge itself be rigid and thus allows the use of flexible materials for the cartridge. It will be appreciated by those of skill in the art that the vacuum chuck needs to be constructed and employed in ways which cause the sample cassette to reproducibly present a consistent optical path through the various sample (and optional calibration) zones. To this end, it is generally desirable to check the degree of vacuum drawn in the vacuum chuck, the spacing of the vacuum zones in the chuck and the like to assure that when the particular sample cassette is placed on the vacuum chuck and there held in place, there is not an unacceptable degree of distortion.

In the embodiment wherein the vacuum chuck and the cassette are used in an optical instrument such as a spectrophotometer, the samples in the cassette may be scanned with a laser and the contents of the sample determined by reference to the fluorescence emanating from the sample. In this case, it is advantageous to minimize background fluorescence, such as fluorescence generated by the materials from which the chuck is fabricated. In this case, it may be advantageous to fabricate the chuck with depressed areas 44 in the form of slots aligned with and directly beneath the optical chambers on the cartridge when the cartridge is placed on the vacuum chuck. Such slots can reduce fluorescence by distancing the material of the chuck from the focal plane of the optical instrument used. In a typical use of the cuvette cartridge, a liquid sample is applied to an inlet hole, thus filling the optical chamber by capillary action. The cartridge is placed in a position for an optical measurement, such as on a platform of a laser scanner. A confocal laser scanner is used to scan the optical chamber. Typically the scanner will utilize the natural fluorescence of the adhesive sheet to define the edges of the optical chamber. In an embodiment, a reference optical chamber can be used by the scanner to detect the edges of the optical chamber. These measurements can then be applied to the optical chambers on the cartridge.

We claim:

1. A cuvette cartridge for optical measurements comprising a flat, adhesive sheet having a selected thickness that defines an optical path length perpendicular to the plane of such flat adhesive sheet; wherein a portion of the adhesive sheet is cut out to define at least two non-communicating optical chambers of a desired length; wherein the adhesive sheet is placed between a first flat sheet and a second flat sheet, the first flat sheet comprising at least two inlet holes and at least two vent holes, each vent hole being located at a first end of one of the optical chambers and each inlet hole being located at a second end of one of the optical chambers.

2. The cuvette cartridge of claim 1, wherein the inlet holes and vent holes for the optical chambers alternate, such that adjacent optical chambers are antiparallel.

3. A disposable optical cuvette cartridge for use in the spectrophotometric analysis of liquid samples, the cuvette cartridge comprising, a pair of parallel sheets of material impermeable to the liquid samples, said two sheets held in spaced relationship to one another by an intermediate layer to which they each are affixed, the intermediate layer having at least one discontinuity defining a sample zone having an optical path defined by the spaced relationship between the two sheets, with at least one of the two sheets being transparent at the wavelength of the spectrophotometric analysis and one of the two sheets carrying an inlet port and a vent port in fluid communication with the sample zone, the spaced relationship being sized to cause capillary action to draw a liquid sample into the sample zone when the sample is placed at the inlet port.

4. The disposable optical cuvette cartridge of claim 3, wherein said intermediate layer comprises a plurality of discontinuities defining a plurality of sample zones each in fluid communication with its individual inlet port and its individual vent port in one of the two sheets.

5. The disposable optical cuvette cartridge of claim 4, wherein said sample zones are elongated with the individual inlet ports and vent ports being at opposite ends of the elongated sample zones.

6. The disposable optical cuvette cartridge of claim 3, wherein the two sheets are each flexible thin films.

7. The disposable optical cuvette cartridge of claim 3, wherein the intermediate layer is a layer of adhesive.

8. The disposable optical cuvette cartridge of claim 3, wherein the intermediate layer itself comprises a flexible thin film.

9. The disposable optical cuvette cartridge of claim 3, wherein the intermediate layer itself comprises a flexible thin film bounded on both sides by layers of adhesive.

10. A method of manufacturing a thin film disposable cuvette cartridge for use in the spectrophotometric analysis of liquid samples comprising:

providing a first flat sheet of flexible film material impermeable to the liquid samples;

providing an intermediate layer also made from a material which is impermeable to the liquid samples;

providing a second flat sheet of flexible film material impermeable to the liquid samples;

said intermediate layer having a thickness preselected to provide a desired spaced relationship between the first and second sheets of flexible film material and having one or more discontinuities which define one or more sample zones having a thickness set by the spaced relationship between the two sheets;

at least one of the first and second sheets being optically transparent at the wavelength employed in the spectrophotometric analysis and one of these two sheets carrying an inlet port and a vent port for each of the sample zones;

the thickness of the intermediate layer defining an optical path through the sample zones and being sized to cause capillary action to draw a liquid sample into one of the sample zones when the sample is placed at its inlet port;

aligning said sheets with said intermediate layer such that the inlet and vent ports are in fluid communication with the sample zones; and sealably bonding said intermediate layer to said first film and said second film.

11. A vacuum chuck for holding a disposable thin film optical cuvette cartridge for use in the spectrophotometric analysis of liquid samples in a flattened and registered position, the cuvette cartridge comprising:

a pair of parallel sheets of material impermeable to the liquid samples, said two sheets held in spaced relationship to one another by an intermediate layer to which they each are affixed, the intermediate layer having at least one discontinuity defining a sample zone having an optical path defined by the spaced relationship between the two sheets, with at least one of the two sheets being transparent at the wavelength of the spectrophotometric analysis and having at least two locating pin holes passing through the pair of parallel sheets and through the intermediate layer;

the vacuum chuck having
a continuous perimeter which is shaped to surround the sample zone when a cuvette cartridge is placed upon it and having additional areas within the perimeter, said perimeter and said additional areas being coplanar and defining a flat planar surface upon which the cuvette cartridge is placed, said flat planar surface having indentations extending below the surface defined by said perimeter and said additional areas, said indentations being located beneath the sample zones when the cuvette cartridge is placed on the chuck, at least two pins extending upwards from said planar surface and located in the planar surface so as to engage the at least two locating pin holes present in the cuvette cassette, and a vacuum source connected to said indentations to apply a vacuum thereto to pull the cuvette cartridge into a locked and registered flat position on the planar surface when the locating pin holes of the cassette are mated with the pins of the chuck.

12. A system for spectrophotometric determination of analyte in liquid samples comprising, an optical cuvette cartridge comprising,
a pair of parallel sheets of material impermeable to the liquid samples, said two sheets held in spaced relationship to one another by an intermediate layer to which they each are affixed, the intermediate layer having at least one discontinuity defining a sample zone having an optical path defined by the spaced relationship between the two sheets, with at least one of the two sheets being transparent at the wavelengths of the spectrophotometric analysis and one of the two sheets carrying an inlet port and a vent port in fluid communication with the sample zone, the spaced relationship being sized to cause capillary action to draw a liquid sample into the sample zone when the sample is placed at the inlet port;

a laser capable of illuminating a sample contained within the sample zone along said optical path and capable of inducing fluorescence from said analyte;

a detector for detecting the fluorescence from said analyte emanating through the transparent sheet and means for reporting the determination of the analyte based upon the fluorescence detected by the detector.

13. The system for spectrophotometric determination of analyte of claim 12, wherein said intermediate layer comprises a plurality of discontinuities defining a plurality of sample zones each in fluid communication with its individual inlet port and its individual vent port in one of the two sheets.

14. The system for spectrophotometric determination of analyte of claim 13, wherein said sample zones are elongated with the individual inlet ports and vent ports being at opposite ends of the elongated sample zones.

15. The system for spectrophotometric determination of analyte of claim 12, wherein the two sheets are each flexible thin films.

16. The system for spectrophotometric determination of analyte of claim 12, wherein the intermediate layer comprises a layer of adhesive.

17. The system for spectrophotometric determination of analyte of claim 16, wherein the intermediate layer is a layer of adhesive.

18. The system for spectrophotometric determination of analyte of claim 16, wherein the intermediate layer itself comprises a flexible thin film bounded on both sides by layers of adhesive.

19. The system for spectrophotometric determination of analyte of claim 16, wherein the laser is a scanning laser.

20. The system for spectrophotometric determination of analyte of claim 19, wherein the adhesive exhibits a second fluorescence distinguishable from the fluorescence of said analyte and said scanning laser is positioned on said sample zone by discriminating between the presence and absence of said second fluorescence and wherein the intermediate layer itself comprises a flexible thin film bounded on both sides by layers of adhesive.

21. A method for spectrophotometric determination of analyte in a liquid sample, comprising:

providing an optical cuvette cartridge comprising:
a pair of parallel sheets of material impermeable to the liquid samples, said two sheets held in spaced relationship to one another by an intermediate layer to which they each are sealably affixed, the intermediate layer having at least one discontinuity defining a sample zone having an optical path defined by the spaced relationship between the two sheets, with at least one of the two sheets being transparent at the wavelengths of the spectrophotometric analysis and one of the two sheets carrying an inlet port and a vent port in fluid communication with the sample zone, placing a drop of said liquid sample on the inlet port and permitting capillary action to draw a liquid sample into the sample zone;

illuminating the sample zone with its liquid sample along the optical path with a laser capable of inducing fluorescence from said analyte;

detecting the fluorescence from said analyte emanating through the transparent sheet and reporting the determination of the analyte based upon the fluorescence detected by the detector.

22. A cuvette cartridge for optical measurements comprising a flat adhesive sheet having a selected thickness that defines an optical path length perpendicular to the plane of such flat adhesive sheet; wherein a portion of the adhesive sheet is cut out to define at least one optical chamber of a desired length;

wherein the adhesive sheet is placed between a first flat sheet and a second flat sheet, the first flat sheet comprising at least one inlet hole and at least one vent hole, the vent hole being located at a first end of the optical chamber and the inlet hole being located at a second end of the optical chamber, wherein at least one dimension of the inlet hole is substantially the same as or larger than at least one dimension of the optical chamber in the plane of the flat adhesive sheet.

* * * * *